United States Patent [19]
Watanabe et al.

[11] Patent Number: 4,695,280
[45] Date of Patent: Sep. 22, 1987

[54] ARTIFICIAL VASCULAR GRAFT

[75] Inventors: Koji Watanabe, Otsu; Miyoshi Okamoto, Takatsuki; Yuichi Mori, Kamakura; Yasuharu Noishiki, Tottori, all of Japan

[73] Assignee: Toray Industries, Inc., Tokyo, Japan

[21] Appl. No.: 910,330

[22] Filed: Sep. 22, 1986

Related U.S. Application Data

[63] Continuation of Ser. No. 617,048, Jun. 4, 1984, abandoned.

[30] Foreign Application Priority Data

Jul. 6, 1983 [JP] Japan ................................ 58-101321

[51] Int. Cl.$^4$ .............................................. A61F 2/06
[52] U.S. Cl. ........................................... 623/1; 623/66
[58] Field of Search ............... 623/1, 11, 66; 26/29 R; 8/130.1; 928/197; 53/425; 210/692

[56] References Cited

U.S. PATENT DOCUMENTS 4,164,045 8/1979 Bokros et al. ........................... 3/1 X
4,445,903 5/1984 Minemura et al. ............... 8/130.1 X

FOREIGN PATENT DOCUMENTS 0057590 8/1982 European Pat. Off. .................. 3/1.4
2744866 11/1978 Fed. Rep. of Germany ........... 3/1.4

Primary Examiner—Richard J. Apley
Assistant Examiner—Alan W. Cannon
Attorney, Agent, or Firm—Wegner & Bretschneider

[57] ABSTRACT

The present invention relates to an artificial vascular graft having ultra fine fibers smaller than 0.5 denier in fineness as part of the inner wall. The artificial vascular graft of this invention is very flexible and produces very low blood leakage. The ease of performing anastomoses is greatly improved. Because of the ultra fine fiber there are many sites to which live cells adhere, the adaptability of the live cells to the fibers of the vascular graft increases, an excellent antithrombotic effect is exerted by the vascular graft, and the formation of the endothelial cells is satisfactory and is observed at a very early stage.

5 Claims, 3 Drawing Figures

ARTIFICIAL VASCULAR GRAFT

This application is a continuation of U.S. application Ser. No. 617,048 filed June 4, 1984, now abandoned.

BACKGROUND OF THE INVENTION

1. Field of the Invention

This invention concerns artificial vascular grafts that provide excellent results in anastomosis, antithrombogenicity and morphology retention.

2. DESCRIPTION OF THE PRIOR ART

Important characteristics for artificial vascular grafts are non-toxicity and non-degradation due to reduction in strength in invivo and the following:

(1) Excellent antithrombotic effect.
(2) Excellent utility for anastomosis.
(3) Excellent morphology retention.

Excellent antithrombogenicity means that the artificial vascular graft forms an intervascular endothelium (a new vascular wall) immediately after implantation.

Conventional artificial vascular grafts are made of woven, knitted or braided polyester fibers which are 1.5 denier or more in fineness.

Conventional artificial vascular grafts are fully and closely interwoven or interknitted to prevent blood leakage through the graft wall and of deformation of the grafts. Consequently, the vascular grafts become very rigid, even though graft softening measures, such as crimping, are taken. This rigidity of the conventional artificial vascular grafts cause a poor penetration of the surgical needle through the graft wall leading to deficiencies which frequently induce a large amount of bleeding in arteriosclerosis.

If the grafts are more loosely woven or braided to improve achievement of anastomosis, the blood leakage becomes severe, especially under administration of anticoagulants.

A further serious problem of conventional grafts is delayed and uneven vascular endothelialization. The thick fibers and dense textures do not provide sites for the endothelialization of such cells. Even when the cells stick to the artificial vascular graft, they are easily washed away due to the dense textural structures. As a result, uniform endothelialization is not produced. In addition, peripheral small vessels are easily obstructed by emboli.

As shown in the Japanese Official Patent Gazette, No. 117287 in 1975; No. 94699 in 1977, and No. 137599 in 1978, loops made on the inner surface of the graft are one way to provide sites for endothelialization. Loops in the conventional grafts, however, provide insufficient sites for cell adhesion, because the loops are fabricated of thick fibers. In addition, the grafts with loops have no satisfactory characteristics for vascular grafts such as ease in penetration of a surgical needle, in anastomosis, satisfactory morphology retention, moderate blood leakage and adaptation to the body. Performing anastomosis and penetration of a surgical needle become difficult when more emphasis is placed on the prevention of blood leakage and morphology retention. When emphasis is placed on functioning in anastomoses and penetration of a surgical needle, prevention of blood leakage and maintenance of the graft shape become difficult. Solving this dilemma has been impossible in the case of conventional vascular grafts.

SUMMARY OF THE INVENTION

The object of this invention is avoidance of the disadvantages of conventional artificial vascular grafts.

With the new artificial vascular grafts of the present invention, intravascular endothelium (the new vascular wall) is formed early and uniformly and the extent of blood leakage is lower. With these new artificial vascular grafts, flattening and collapsing do not occur during and after the surgical operation.

It is, therefore, well-suited for use in performing anastomosis to a living graft. Thus, the present invention provides the highest quality of artificial vascular grafts that has been made to date. This vascular graft has some very fine fibers of less than 0.5 denier, as at least part of the inner wall. The minimum fineness is limited by provision of adequate structural strength. Fineness less than 0.0001 denier will thus be less desirable.

DESCRIPTION OF THE PREFERRED EMBODIMENTS

Figure 1:
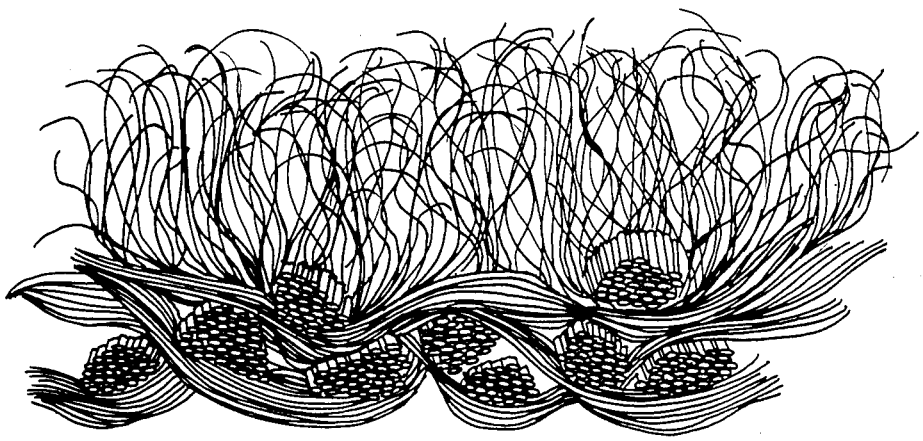
FIG. 1 is a representation of a magnified cross-sectional view of an artificial graft prepared according to the procedures of Examples 1.
Figure 2:
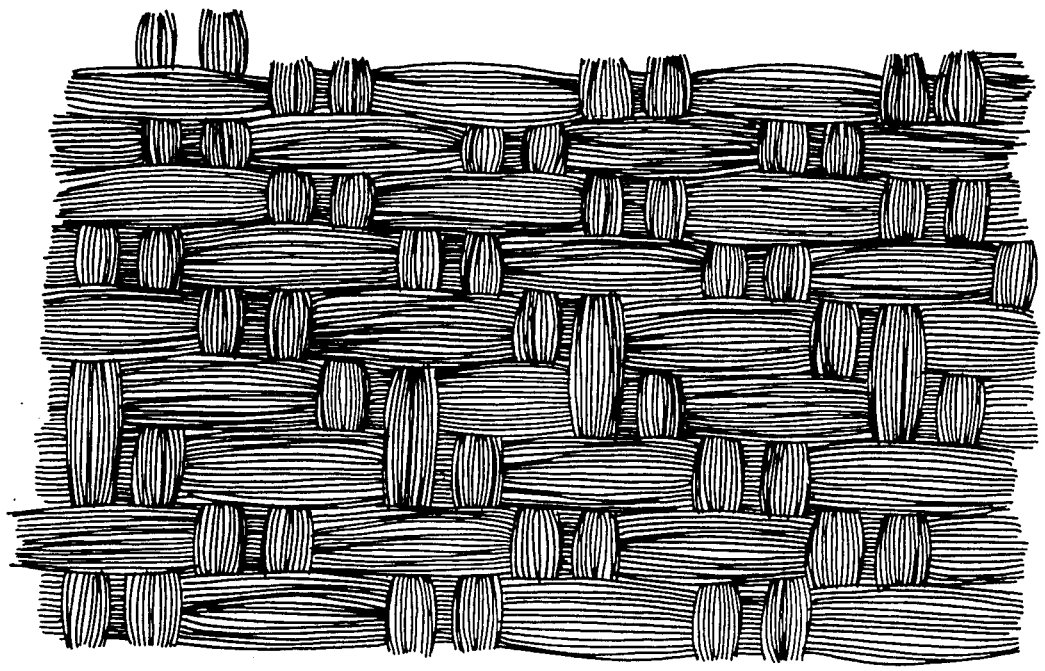
FIG. 2 is a representation of the structure of a commercially accepted vascular graft known under the name "Cooley Graft".
Figure 3:
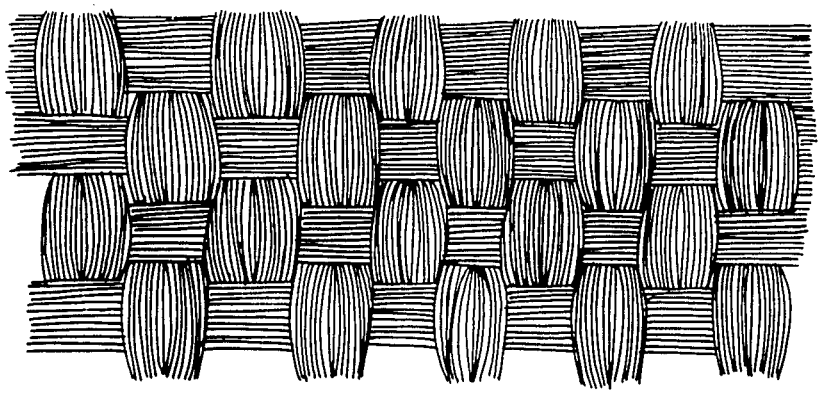
FIG. 3 is a representation of the weaving structure of Example 3 of this application.

In manufacturing the artificial vascular graft relating to this invention conventional processes such as weaving, knitting and braiding are adopted to get the graft with the intended inner diameter and fabric density even though ultra fine fibers are used.

The term "ultra fine fiber" means a fiber less than 0.5 denier, and preferably 0.3 or less, including synthetic, reclaimed, and various other types of fiber. It is possible to use ready-made very ultra fine fiber in making artificial vascular grafts. But a more preferable way of making the grafts comprises used very ultra fine fibers of a special type that is composed of a plurality of fiber components and can be made into fibrils or very ultra fine fibers by removing or stripping at least one component of the fiber.

Such fibers are known, for example, from U.S. Pat. No. 3,531,368 and the Japanese Official Patent Gazette No. 22126 in 1973, No. 22593 in 1978 and elsewhere. Using such a special type of fibers difficulties relating to the minuteness of fibers in the process (such as breaking and napping of the fibers during weaving, knitting or braiding) can be minimized because the thickness of the fibers can be kept at ordinary dimension until completion of the tube formation for the graft and because the fibers can be made very minute in the tube (graft) avoiding troubles during the process resulting from the minuteness of fibers.

The ultra fine fiber, in this invention, means a fiber of less than 0.5 denier, preferably 0.3 or less. Artificial vascular grafts made of such ultra fine fibers provide good flexibility, good anastomosis, remarkable decrease of blood-leakage, and enhancement of adherence of living cells to the wall of the graft and adaption of the cell to the fibers, that is to say good and rapid formation of endothelial cells.

As a result such an artificial vascular graft is strongly antithrombotic.

Polymers used for the vascular grafts are polyesters, polyamides, polyurethanes, or polyolefins, Polyester is generally most suitable. When the special type of fibers composed of a plurality of components is used, components to be retained are selected from the polymers mentioned above and other components to be removed or stripped are, for example, polystyrene, polyolefin, polyamide (preferably water-soluble polyamide), water-soluble polyvinyl alcohol, or copolyester, such as those comprising sulfacodium-isophthalate or polyethylene glycohol.

The choice of polymers is not only limited to these suggestions and should be made considering spinnability, process, function, etc. When grafts are produced using the method presented by this invention, ordinary systems for forming tubes as weaving, knitting and braiding can be effectively used.

In manufacturing conventional artificial vascular grafts, fibers having ordinary thick deniers are used so that the products are very stiff and not flexible to a satisfactory extent. Thus, the texture of the graft should be relatively rough or open to prevent such stiffness. However, rough textures of the artificial grafts allow blood leakage, especially when anticoagulants are given.

On the other hand, close textures of the artificial grafts prevent the formation of intravascular endothelium, thus resulting in poor performance. The artificial vascular grafts relating to the present invention comprise very minute fibers so that the grafts are kept soft and flexible even if their texture is made close. In addition, as the fibers of the grafts become more minute tne cells become more adaptable to the fibers. The fiber texture best for manufacturing of artificial vascular grafts cannot be decided beforehand because the specific requirements differ with the specific use.

It is convenient to refer to the rate of water permeation as a standard measure. The phrase rate of water permeation, is defined here as the amount (ml/minute) of water permeating through 1 $cm^2$ of the surface of the grafts (or cloth) under 120 mm Hg of pressure.

To prevent blood leakage, this rate should be below 500 ml/min, and preferably below 100 ml/min. These values are only guides and it is unnecessary to adhere to them strictly. There may be many cases where artificial vascular grafts of this invention have rates of water permeation of 3000 and 5000 ml/min but are superior to conventional artificial vascular grafts in formation of intervascular endothelium and in utility for anastomosis. But performance of the artificial vascular grafts is particularly good when the rate of water permeation is low.

To obtain the same rate of water permeation using fibers of ordinary denier, the texture must be dense. The very minute fibers of the grafts relating to this invention do not hinder the formation of endothelial cells, even when the rate of water permeation is less than 500 ml/min, probably because of the adaptability of the cells to the fibers.

As mention above, the artificial vascular graft comprising very minute fibers is soft, flexible and allows excellent penetration of a surgical needle in spite of a dense texture.

In addition, formation of intervascular endothelial cells (a new vascular wall) is surprisingly rapid and uniform. Although the effects on cell formation cannot be fully explained, fibrin deposition on the wall of the graft can be assumed to be of vital importance for cell formation. By the adoption of very minute fibers, a large number of microgaps among the fibers are formed which allow cell and fibrin to enter more easily.

Thus, it appears that fibrin deposition is very uniform, thin and consolidated when very minute fibers are used. When such fibers are used for both inner and outer walls of the graft, the adaptability of the graft to the surrounding tissues is promoted. Sometimes this quality is unnecessary for the outer wall of the graft. When the structure of the graft made as described here is made multiple by the combined use of very minute fibers (A) and fibers of 1.0 denier or more (B), the grafts show better performahce. In particular, employment of the fibers (B) not only prevents deformation of the artificial vascular grafts but also enhances cell formation.

In preparing grafts according to the preseht invention, such multiple structures are recommended as: double-weft structure, double-warp structure, double-warp and-weft structure, triple or greater warp and weft structure, weft pile structure, warp pile structure, a structure produced by the application of these structures, cut pile of these structures, and fabrics produced by combining these structures. These fabric structures are obtained by weaving these structures. These fabric structures are obtained by weaving or knitting, preferably tricotting to prevent ravelling of the graft. The prefered fabric structure by tricotting are, for example, half stitch, dembigh-stitch, satine-stitch, with or without piles or naps.

The braid of the present invention is easily produced by using braid structures that can be combined in the same way as for the textiles or knit fabrics. The combinations of the fibers in multiple structures are as follows: (1) for front (facing) structure, only ultra fine fibers (A) or a mixture of very minute fibers (A) and fibers (B), (2) for back (base) structure, only fibers (B), a mixture of fibers (A) and fibers (B) or only fibers (A). The artificial vascular graft of the present invention is obtained more simply and more conveniently by using sheath-core type yarns. The sheath-core type yarn means that fibers (B) as core yarns are covered with fibers (A) as sheath yarns.

With such yarns, the inner and the outer wall of the vascular graft-are covered with ultra fine fibers, and morphology retention of the vascular graft is improved.

It is necessary that at least the inner wall of the artificial vascular grafts according to the present invention has the front (facing) structure, while the outer wall and/or the so-called medial wall between the inner and outer walls have back (base) structures. The yarn constituting the ground structure is called base yarn or core yarn. Sometimes, the base structure itself is called the lining structure.

Dimensional stability and performance of the artificial grafts are much improved by selection of these multiple fabric structures and combinations of fibers, that is to say, by using, for example, fibers (A) which are effective in formation of endothelial cells for front and/or back structure, and fibers (B)/and fibers (A) for back structures.

The artificial graft having such structures has good needle-penetrability and flexibility at the same time.

The ultra fine fibers (A), and (B) are used in filament or staple yarn, preferable in filament yarn because of smaller possibility of fluff drop-outs into blood when put to use for the grafts. The fibers (B) are of 1.0 denier or more, preferably 1.3 denier or more.

Furthermore, fibers (B) are preferably bulk-processed by false-twisting. Other type of fibers (B) are latent crimp fibers such as side-by-side type composite fibers, eccentrically arranged composite fibers, or wooly-processed fibers.

The artificial vascular graft could be made by cutting a piece of cloth and sewing, adhering or fusing it into a tube.

However, a preferred way of making it is to make directly a jointless tube for the graft out of fibers. When the tube is made of the special type of fibers which comprise a plurality of components, the tube is treated by a chemical reagent to remove or to separate other components out of the fiber so that the fiber is transformed into ultra fine fibers.

In order to make the present invention more effective, it is recommendable to raise naps of the ultra fine fiber (A) on the inner and outer walls. This is especially effective when mixed yarn of fibers (A) and fibers (B) is used. When fibers (A) are used solely, performance of the artificial vascular is found to be good enough so that it is not necessary to raise naps of ultra fine fibers on the walls of the graft.

The term naps of fiber as used herein, means loop-naps, cut-naps, raised naps or the like. The naps of fiber are formed by making loop-naps or out-naps directly on tube (graft) fabrication, applying such ordinary weaving or knitting technologies, or by raising naps after tube (graft) fabrication with a raising machine or bulling machine.

Although the state of naps of fiber is adjustable according to the purpose, the unexpected effect of the present invention is shown by the fact that performance of the graft does not fluctuate comparatively in the presence of non-uniformity in length and direction of naps of fibers. This is attributed to the remarkable effect of naps of very minute fibers.

EXAMPLE 1

An artificial vascular graft (inside diameter; 18 mm) of plane structure was woven with the following yarns:

Warps of false-twisted polyethylene terephthalate yarn (75 denier, 36 filaments); Wefts of the special type of composite fibers (Japanese Patent No. 22126 of 1973) which are composed of 85 parts of polyethylene terephthalate (as 145 filamentary island components) and 15 parts of polystyrene (as sea component) and which are of 170 denier and 60 filaments.

This tube was immersed in trichloroethylene to remove polystyrene. The tube was dried and pierced by a steel stick (outside diameter: 16 mm) with a spiral screw of 3 mm pitch. Then, steel wire was wound along the screw bezel covered with the tube. The tube was heated at 180° C. for 3 minutes in that state. Then the tube was detached from the steel stick. This tube was very flexible, though the rate of water permeation was only 73 ml/min.

This tube was implanted as an artificial vascular graft into the descending aorta of a dog, and performance was examined. Prior to the implantation, the artificial vascular graft was cut with a surgical laser ray scalpel to the correct length. At this time, partial fusions of fibers or partial adhesions took place among the out ends of polyethylene terephthalate fibers. By these partial adhesions, the artificial graft was prevented from hardening and ravelling at the cut end.

The performing of anastomosis was extremely easy due to the excellent flexibility of the artificial vascular graft. Tests showed that blood leakage was very slight at the initial stage following the operation. About 3 months later, the neo-intima composed of living cells was completely formed in the inner wall of the artificial vascular graft.

EXAMPLE 2

A tube (graft) was produced using composite fibers (described in U.S. Pat. No. 3,531,368) of 150 denier and 42 filaments composed of 50 parts of polyethylene terephthalate (as 16 island components) and 50 parts of polystyrene (as sea component) for front structure, and 75 denier 36 filament yarn of polyethylbutylene terephthalate for back (ground) structure by tricot satin technique.

The tube was shrunk in hot water and immersed in trichlorethylene after drying. The tube was turned inside out after drying and its surface was scrubbed with raising machine to raise naps of ultra fine fibers. The tube was then washed thoroughly with water for 20 minutes. After drying, the tube was again turned inside out and sterilized using ethylene oxide gas.

The rate of water permeation through the fabric was 63 ml/min. Such tubes, as artificial vascular grafts, were implanted into the descending aorta of dogs.

The suturing of the graft to a live vascular graft was easily performed and very satisfactory. No blood leakage was noted, although preclotting was not performed before the operation.

However, blood could infiltrate into the whole fabric. Observation of excised specimens revealed the following: some 21 days after the implantation, formation of the neo-intima was marked; 2 months after the implantation. formation of the neo-intima was very active, and furthermore, swelling-like granulation tissue or intimal hypertrophic swelling containing many vessels developed in the internal surface of the graft; and 85 days after the implantation, the neo-intima on the inner wall of the graft was completely formed, which was glossy and grayish-white.

These results suggest that the healing process was significantly shortened compared with that of the conventional vascular grafts.

EXAMPLE 3

A graft (inside diameter of 17 mm; length of 100 cm) was produced by using the following materials and methods. The warps and wefts (ground and lining yarn) used were false-twisted polyethylene terephthalate yarn (50 denier, 24 filaments) and the front wefts used were complex fibers (U.S. Pat. No. 3,531,368) the components of which were 78 parts of polyethylene terephthalate (as the island-type ingredient), 22 parts of polystyrene (as the sea-type ingredient), and 36 island-type fibers (245 denier, 40 filaments).

These materials were woven into a double warp and weft textile shaped like a tube. The tube was washed with hot water and dried. After drying, polystyrene was removed by means of perchlorethylene. Then, the tube was napped using a napping machine. The napped tube was washed with hot water, dried, turned inside out, and sterilized by use of ethylene oxide gas.

The sterilized graft was implanted into the descending aorta of a dog. The rate of water permeation through the cloth was 295 ml/min. In implanting the tube into the aorta, suturing of the tube to the live vascular graft was performed easily and satisfactorily. In particular, the needle penetrability was good. Owing to the flexibility of the tube, the sutures were effective and the anastomosis was satisfactorily performed.

Although preclotting was not performed before the operation, because of the low rate of water permeation, blood leakage was very slight. Blood infiltrated into the whole cloth, which turned reddish. Observation of excised specimens of the artificial vascular graft from several such operations revealed the following: the red color seen immediately after the implantation faded, turning light red in 2 days; blood infiltration decreased, with a marked formation of the neo-intime, 20 days after the implantation; a swelling like that of granulation tissue, indicating a very active formation of the neo-intima, developed 2 months or longer after, the implantation; and the formation of the neo-intima on the inner wall of the vessel was almost completed, the color of the neo-intima being grayish-white, about 3 months after the implantation.

These results indicated that the healing process was significantly shortened compared with that conventional artificial vascular grafts.

What is claimed is:

1. An artificial vascular graft fabric consisting essentially of
   (a) ultra-fine fibers of less than 0.5 denier, and
   (b) conventional denier fibers of more than 1.0 denier, wherein said fibers are braided, woven or knit to form said artificial vascular graft fabric, whereby said artificial vascular graft fabric has at least a first inner surface and a second outer surface, said first inner surface consisting essentially of ultra-fine fibers.

2. An artificial vascular graft as defined in claim 1 wherein said conventional denier fibers comprise a ground weave.

3. An artificial vascular graft fabric as defined in claim 1 wherein said ultra-fine fibers of said first inner surface are napped.

4. An artificial vascular graft as defined in claim 1, wherein said ultra fine fibers are made from polymers selected from the group consisting of polyester, polyamide, and polyolefin.

5. An artificial vascular graft as defined in claim 1, wherein said artificial vascular graft has water-permeation rates not greater than 500 ml/min.

* * * * *